(12) United States Patent
Wu et al.

(10) Patent No.: US 8,092,835 B1
(45) Date of Patent: Jan. 10, 2012

(54) INJECTABLE MICROSPHERES

(75) Inventors: Daqing Wu, Ithaca, NY (US);
Chih-Chang Chu, Ithaca, NY (US);
Joseph Carozza, Southport, CT (US)

(73) Assignee: Cytogel Pharma, LLC, Darien, CT (US)

( * ) Notice: Subject to any disclaimer, the term of this patent is extended or adjusted under 35 U.S.C. 154(b) by 0 days.

(21) Appl. No.: 13/269,738

(22) Filed: Oct. 10, 2011

Related U.S. Application Data

(63) Continuation of application No. 13/015,193, filed on Jan. 27, 2011, now Pat. No. 8,034,383, which is a continuation of application No. 11/148,662, filed on Jun. 9, 2005, now abandoned.

(60) Provisional application No. 60/582,824, filed on Jun. 28, 2004.

(51) Int. Cl.
*A61K 9/14* (2006.01)
(52) U.S. Cl. ........ 424/489; 424/469; 528/271; 528/302; 528/354; 528/361
(58) Field of Classification Search .................. None
See application file for complete search history.

(56) References Cited

U.S. PATENT DOCUMENTS

| | | | |
|---|---|---|---|
| 4,663,160 A | 5/1987 | Tsay et al. | |
| 5,410,016 A | 4/1995 | Hubbell et al. | |
| 6,107,358 A | 8/2000 | Harada et al. | |
| 6,592,895 B2 | 7/2003 | Lang et al. | |
| 7,670,616 B2 | 3/2010 | Wu et al. | |
| 2003/0147835 A1 | 8/2003 | Munro et al. | |
| 2006/0013886 A1 | 1/2006 | Wu et al. | |
| 2007/0207213 A1 | 9/2007 | Chu et al. | |

FOREIGN PATENT DOCUMENTS

| | | |
|---|---|---|
| WO | WO 00/60956 | 10/2000 |

OTHER PUBLICATIONS

Border et al., "Induction of Membranous Nephropathy in Rabbits by Administration of an Exogenous Cationic Antigen", *The Journal of Clinical Investigation*, Feb. 1982, vol. 69, No. 2, pp. 451-461.
Cho et al., "Clonazepam release from bioerodible hydrogels based on semi-interpenetrating polymer networks composed of poly($\epsilon$-caprolactone) and poly(ethylene glycol) macromer", *International Journal of Pharmaceutics*, 1999, vol. 181, No. 2, pp. 235-242.
Cruise et al., "Characterization of Permeability and Network Structure of Interfacially Photopolymerized Poly(ethylene glycol) Diacrylate Hydrogels", *Biomaterials*, Jul. 1998, vol. 19, No. 14, pp. 1287-1294.
Heller et al., "Injectable Semi-Solid Poly (Ortho Esters) for the Controlled Delivery of Therapeutic Agents: Synthesis and Applications", *Drug Delivery Technology*, 2002, vol. 2, No. 1, pp. 1-11.
Jeong et al., "Thermoreversible gelation of PEG-PLGA-PEG triblock copolymer aqueous solutions", *Macromolecules*, 1999, vol. 32, No. 21, pp. 7064-7069.
Kim et al., "Methoxy Poly(ethylene glycol) and $\epsilon$-caprolactone Amphiphilic Block Copolymeric Micelle Containing Indomethacin. II. Micelle Formation and Drug Release Behaviours", *Journal of Controlled Release*, Jan. 1998, vol. 51, No. 1 pp. 13-22.
Lang et al., "Synthesis and Structural Analysis of Functionalized Poly($\epsilon$-Caprolactone)-Based Three-Arm Star Polymers", *Journal of Polymer Science Part A: Polymer Chemistry*, 2002, vol. 40, No. 8, pp. 1127-1141.
Peppas et al, "Hydrogels in Pharmaceutical Formulations", *European Journal of Pharmaceutics and Biopharmaceutics*, Jul. 2000, vol. 50, No. 1, pp. 27-46.
Price, "Micelle Formation by Block Copolymers in Organic Solvents", *Pure and Applied Chemistry*, 1983, vol. 55, No. 10, pp. 1563-1572.
Qiu et al., "Miscibility and crystallization of poly(ethylene oxide) and poly($\epsilon$-caprolactone) blends", *Polymer*, 2003, vol. 44, No. 10, pp. 3101-3106.
Wu et al., "Synthesis, Characterization and Drug Release from Three-Arm Poly($\epsilon$-Caprolactone) Maleic Acid/Poly(ethylene glycol) Diacrylate Hydrogels", *Journal of Biomaterials Science. Polymer Ed.*, Aug. 2003, vol. 14, No. 8, pp. 777-802.
Youan et al., "Evaluation of Sucrose Esters as Alternative Surfactants in Microencapsulation of Proteins by the Solvent Evaporation Method", *AAPS PharmSci*, 2003, vol. 5, No. 2, article 22, pp. 1-9.

*Primary Examiner* — Robert A Wax
*Assistant Examiner* — Hasan Ahmed
(74) *Attorney, Agent, or Firm* — Saliwanchik, Lloyd & Eisenschenk

(57) ABSTRACT

Injectable microspheres are obtained from double bond functionalized polyhydric alcohol ester by a method comprising dissolving the double bond functionalized esters in a hydrophobic organic solvent, forming an aqueous solution of stabilizer, forming an oil in water emulsion where the solution of stabilizer constitutes the continuous phase and the solution of ester constitutes the disperse phase and evaporating the organic solvent or from block copolymer of PGCLM and methoxy poly(ethylene glycol).

16 Claims, 1 Drawing Sheet

INJECTABLE MICROSPHERES

CROSS-REFERENCE TO RELATED APPLICATION

This application is a continuation application of co-pending Application Ser. No. 13/015,193, filed Jan. 27, 2011 now U.S. Pat. No. 8,034,383; which is a continuation application of application Ser. No. 11/148,662, filed Jun. 9, 2005, now abandoned; which claims priority to U.S. Provisional Application Ser. No. 60/582,824, filed Jun. 28, 2004, all of which are incorporated by reference herein in their entirety, including any figures, tables, or drawings.

TECHNICAL FIELD

This invention is directed at materials and methods for forming injectable hydrogel microspheres and at the microspheres formed there from that can be used to load drugs and other biologically active agents and are useful for controlled release of these in the body.

BACKGROUND OF THE INVENTION

Microspheres with encapsulated or covalently bonded biologically-active agent allow provision of an injectable suspension as a substitute for surgical implantation and facilitate administration of multiple drugs in a single injection. These microspheres provide an initial burst to reach a therapeutic concentration followed by a zero-order release of drug to maintain the therapeutic level by compensating for metabolic loss. The microspheres thus provide a sustained release therapeutic concentration.

Microspheres of biodegradable polyesters from D,L-lactide/glycolide and microspheres of biodegradable polyesters from ε-caprolactone have received attention for controlling release in the body of pharmaceutical agents and macromolecules. However, these polyesters are relatively hydrophobic and a more hydrophilic surface is desirable on an injectable microsphere to increase effective lifetime in the circulatory system and to reduce the occurrence of an inflammatory response. Hydrophilic characteristics have been achieved by surface modification of the polyester microspheres with hydrophilic polymers. Polyester microspheres with more hydrophilic surfaces have not heretofore been obtained without relying on chemical attachment or physical absorption of hydrophilic polymers.

BRIEF SUMMARY OF THE INVENTION

The subject invention provides unique and advantageous biodegradable injectable polyester microspheres. The microspheres of the subject invention can be prepared with surface hydrophilicity, but without the requirement of surface modification with a hydrophilic polymer. In a preferred embodiment the microspheres are formed from a double bond functionalized polyhydric alcohol ester of polyester.

In one embodiment, the subject invention provides biodegradable microspheres from multiarm synthetic biodegradable polymers. Specifically, a novel drug carrier composed of double-bond-functionalized glycerol poly(ε-caprolactone) maleic acid (PGCLM) microspheres can be prepared by an emulsification-solvent evaporation technique. The microspheres have unsaturated C═C double bonds on the surface. The availability of this chemical functionality on the microsphere surface provides enormous potential for altering the surface chemistry of the microspheres to tailor to specific clinical applications. For example, the C═C double bonds can be used to render a hydrogel network surface on these microspheres via a photo-crosslinking treatment. The resulting microspheres then have two very different compartments: a hydrogel surface with a non-hydrogel core. Different drugs can be incorporated into different compartments for customized target release.

In a specific embodiment, an ovalbumin (OA) protein was pre-loaded into the synthetic biodegradable microspheres of the subject invention and its release was examined. The microspheres were characterized in terms of their morphology, size distribution, drug loading efficiency and stability. Results shown that OVA was successfully entrapped inside the microspheres with loading efficiency up to 45% (w/w) and loading level 8.1%. The cumulative OVA release % (w/w) reached around 40% at 37° C. in 50 days.

In one embodiment, the subject invention is directed to forming a biodegradable injectable microsphere by a method comprising the steps of (a) dissolving a double bond functionalized polyhydric alcohol ester of polyester in a hydrophobic organic solvent, (b) dissolving a stabilizer in water, (c) admixing the solutions formed in step (a) and step (b) to form an emulsion where the solution formed in step (b) constitutes the continuous phase and the solution formed in step (a) constitutes the disperse phase, (d) evaporating the organic solvent to form a hardened microsphere by polymer precipitation, from the double bond functionalized polyhydric alcohol ester, (e) recovering the microsphere.

In one embodiment, the double bond functionalized polyhydric alcohol esters are obtained by polymerizing ε-caprolactone monomer or a blend of ε-caprolactone and lactide monomer or glycolide monomer in the presence of a polyhydric alcohol containing from 3 to 6 hydroxyl groups to form a polyhydric alcohol ester where the acyl groups contain free hydroxyl as their terminal ends and reacting with maleic anhydride to convert some or each of the free hydroxyls to moiety containing 2-carboxy ethenyl group.

In another embodiment, denoted the second embodiment of the invention, the invention is directed to a biodegradable injectable microsphere having a mean transverse dimension ranging from about 15 to 60 μm, formed of hardened double bond functionalized polyhydric alcohol ester of polyester and loaded with from about 1 to 10% by weight of the microsphere of a drug or other biologically active agent for sustained release after injection of the microsphere into an animal. The release can take place over a period ranging up to a few months.

The double bond functionality allows covalent bonding to biologically active agents for delayed release as well as provides the opportunity to form a hydrogel at the microsphere surface. This provides the advantage of allowing two different release modes, one from with the microsphere and the other from within the hydrogel.

In one embodiment, the double bond functionalized polyhydric alcohol ester is obtained by polymerizing ε-caprolactone monomer in the presence of glycerol to form polyhydric alcohol ester where the acyl groups contain free hydroxyl at their terminal ends and reacting with maleic anhydride to convert some or each of the free hydroxyls to a moiety containing a carboxy ethenyl group.

In another embodiment, denoted the third embodiment of the invention, amphiphilic plural block copolymers where one block is from a polymer obtained by polymerizing ε-caprolactone monomer in the presence of glycerol to provide esters with free hydroxyl at the terminal ends of the acyl groups and reacting with maleic anhydride to convert some or each of the free hydroxyls to a moiety containing a 2-carboxy ethenyl group and the other block(s) are from methoxy poly (ethylene glycol), are used to form loaded microspheres by dissolving the plural block copolymer in a solvent that does not dissolve the drug (or other bioactive agent) and adding the drug (or other bioactive agent).

DETAILED DESCRIPTION

Figure 1:
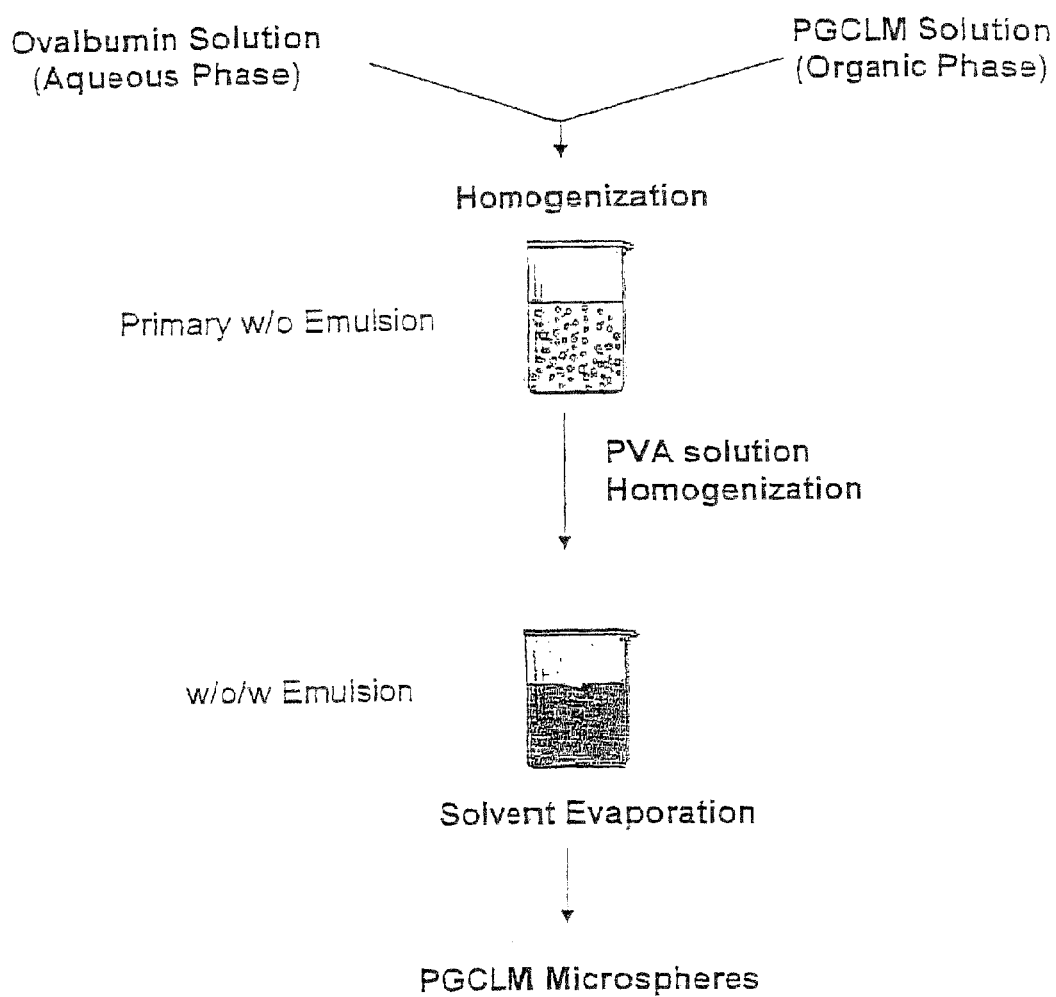
FIG. 1 shows a diagram of the preparation of poly(glycerol-co-caprolactone) maleic acid (PGCLM) microspheres with entrapped protein ovalbumin.

The subject invention provides unique and advantageous biodegradable injectable microspheres. The properties of the microspheres of the subject invention can be modified as described herein in order to give characteristics that are advantageous for particular uses.

In one preferred embodiment, the surface of the microspheres is hydrophilic. In another embodiment, the microspheres have a hydrogel formed at the surface. Advantageously, the microspheres can be utilized to deliver biologically active agents to a desired site. Furthermore, the rate of release of the active agent(s) can be carefully controlled as described herein.

A further advantage of the microspheres of the subject invention pertains to the use of sucrose esters and dextran in order to reduce toxicity associated with previously-known microspheres.

In a preferred embodiment the microspheres are formed from a double bond functionalized polyhydric alcohol ester of polyester.

In one embodiment, the subject invention is directed to forming a biodegradable injectable microsphere by a method comprising the steps of:
(a) dissolving a double bond functionalized polyhydric alcohol ester of polyester in a hydrophobic organic solvent,
(b) dissolving a stabilizer in water,
(c) admixing the solutions formed in step (a) and step (b) to form an emulsion where the solution formed in step (b) constitutes the continuous phase and the solution formed in step (a) constitutes the disperse phase,
(d) evaporating the organic solvent to form a hardened microsphere by polymer precipitation, from the double bond functionalized polyhydric alcohol ester,
(e) recovering the microsphere.

In one embodiment, the double bond functionalized polyhydric alcohol esters are obtained by polymerizing ε-caprolactone monomer or a blend of ε-caprolactone and lactide monomer or glycolide monomer in the presence of a polyhydric alcohol containing from 3 to 6 hydroxyl groups to form a polyhydric alcohol ester where the acyl groups contain free hydroxyl as their terminal ends and reacting with maleic anhydride to convert some or each of the free hydroxyls to moiety containing 2-carboxy ethenyl group.

In another embodiment, denoted the second embodiment of the invention, the invention is directed to a biodegradable injectable microsphere having a mean transverse dimension ranging from about 5 to 200 µm and, more specifically, 15 to 60 µm, formed of hardened double bond functionalized polyhydric alcohol ester of polyester and loaded with from about 0.1 to 25% and, more specifically, 1 to 10% by weight of the microsphere of a drug or other biologically active agent for sustained release after injection of the microsphere. The release can take place over a period ranging up to a few months.

The double bond functionality allows covalent bonding to biologically active agents for delayed release as well as provides the opportunity to form a hydrogel at the microsphere surface. This provides the advantage of allowing two different release modes, one from with the microsphere and the other from within the hydrogel.

In one embodiment, the double bond functionalized polyhydric alcohol ester is obtained by polymerizing ε-caprolactone monomer in the presence of glycerol to form polyhydric alcohol ester where the acyl groups contain free hydroxyl at their terminal ends and reacting with maleic anhydride to convert some or each of the free hydroxyls to a moiety containing a carboxy ethenyl group.

In another embodiment, denoted the third embodiment of the invention, amphiphilic plural block copolymers where one block is from polymer obtained by polymerizing ε-caprolactone monomer in the presence of glycerol to provide esters with free hydroxyl at the terminal ends of the acyl groups and reacting with maleic anhydride to convert some or each of the free hydroxyls to a moiety containing a 2-carboxy ethenyl group and other block (s) are from methoxy poly (ethylene glycol), are used to form loaded microspheres by dissolving the plural block copolymer in a solvent that does not dissolve the drug (or other bioactive agent) and adding the drug (or the bioactive agent).

The double bond functionalized polyhydric alcohol esters of polyesters for step (a) include those described in Lang, M., et al, Journal of Polymer Science: Part A: Polymer Chemistry, Col 40, 1127-1141 (2002) and can be synthesized as indicated therein.

Double bond functionalized polyhydric alcohol esters of polyesters can be obtained by polymerizing ε-caprolactone monomer in the presence of glycerol to provide esters with free hydroxyl at terminal ends of the acyl groups and reacting with maleic anhydride to convert some or each of the free hydroxyls to moiety containing 2-carboxy ethenyl group. Examples of such compounds and their preparation are described in U.S. Pat. No. 6,592,895 and may be referred to herein as PGCLM. The resulting compounds have an average molecular weight, $M_n$, ranging for example, from 1,000 to 50,000.

Another embodiment is a double bond functionalized poly (ortho esters) prepared by the reaction between the diketene acetal 3,9-diethylidene-2,4,8,10 tetraoxaspiro[5.5] undecane and 1,10-decanediol (triethylene glycol can also be used to replace 1,10 decanediol). Molecular weights can be tailored by using n-decanol to act as a chain regulator.

The poly (ortho esters) can be prepared by the addition of diols triethylene glycol or 1,10-decanediol to 3,9-diethylidene-2,4,8,10 tetraoxaspiro[5.5] undecane. These polymers can be prepared by dissolving the reagents in tetrahydrofuran and adding a trace of an acid catalyst.

A significant advantage of this polymer system is that the nature of the diols controls the mechanical properties of the polymer so that materials ranging from hard to soft flexible materials can be made.

The solvent for step (a) is one that dissolves the double bond functionalized polyhydric alcohol ester of polyester at room temperature and that has a boiling point ranging, for example, from 30-45° C. (which allows for easy removal of solvent). A preferred solvent for step (a) is dichloromethane (bp of 38.9-40° C.). Other suitable solvents for step (a) include chloroform, ethyl acetate, and N,N-dimethylformamide.

For step (a), the double bond functionalized polyhydric alcohol esters of polyesters are dissolved in the hydrophobic organic solvent in an amount ranging, for example, from 0.5 to 10% w/v. An increase in concentration causes an increase in mean diameter of the microsphere ultimately obtained as well as in loading efficiency of water soluble drug loaded as described hereinafter and at least up to 6% w/v causes an increase in loading level (drug %, w/w of microsphere).

The stabilizer for step (b) is a compound that is essentially insoluble in the solvent of step (a), is removable by washing with water, is stable in sunlight and artificial light, reduces the interfacial tension between aqueous and organic phases and limits collapse of droplets formed in step (c) before hardened microspheres are obtained.

A preferred stabilizer is a sucrose ester for the microencapsulation of PGCLM by the Solvent Evaporation Method. This is a deviation from conventional microencapsulation processes using the surfactant PVA solvent in the evaporation technique. PVA has severe limitations due to its relative toxicity. Advantageously, sucrose-based surfactants are biodegradable surfactants whose hydrophilic and lipophilic properties can be adjusted by varying fatty acid chain lengths. Examples of sucrose-based surfactants include:

Sucrose Esters:
Sucrose Monooleate
Sucrose Monolaurate
Sucrose Mono-ester: 1 mole of fatty acid with 1 mole sucrose
Di-ester 2 moles of fatty acid
Tri-ester 3 moles of fatty acid
Other stabilizers include Pluronic F68 (ethylene oxide/propylene oxide block copolymer having the structure:

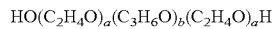

where a is 80 and b is 27, having a molecular weight ranging from 7680 to 9510 (and CAS Registry Number 9003-11-6), human serum albumin (HSA), sodium chlorate, and charged and uncharged dextran (weight average molecular weight ranging from 40,000 to 80,000).

Methods relevant to the practice of the subject invention can be found at, for example, (Heller J. et al. (2002) "Injectable Semi-Solid Poly (Ortho Esters) for the Controlled Delivery of Therapeutic Agents: Synthesis and Application" *Drug Delivery Technology* Vol. 2(1): 1-11 and Youan et al. (2003) "Evaluation of Sucrose Esters as Alternative Surfactants in Microencapsulation of Proteins by the Solvent Evaporation Method" *AAPS PharSci* Vol. 5(2): 1-7).

As noted above, a less preferred stabilizer is polyvinyl alcohol (PVA) having a number average molecular weight ranging from 10,000 to 30,000 which is 85-90% hydrolyzed and is present in the solution formed in step (b) in amount ranging from 0.5 to 10%, w/v.

The volume ratio of solution formed in step (b) to solution formed in step (a) admixed in step (c) can range, for example, from 3:1 to 10:1. Admixing can be carried out at 800 to 1,000 rpm for 5 minutes to 1 hours using a magnetic stirrer.

The evaporation of step (d) is readily carried out with stirring while exposing the emulsion formed in step (c) to the atmosphere while maintaining the emulsion at room temperature to 45° C. Upon evaporation the microspheres precipitate and become hardened because of the greater presence of stabilizer at the surface of emulsion droplets.

The recovery of step (e) may be affected by centrifuging to collect the microspheres, washing the microspheres with distilled water to remove emulsifier, freeze drying and then storing until used.

In one embodiment of the subject invention, the surface of a microsphere is converted to a hydrogel. This is effected by including a photoinitiator in the solution formed in step (a), e.g, at a level of about 0.05 to 0.5% w/w of the double bond functionalized polyhydric alcohol ester, e.g., 2,2-dimethoxy 2-phenyl acetophenone (DMPA) at a level of about 0.1% (w/w of PGCLM), and then admixing the solutions formed in step (a) and step (b) to form the emulsion of step (c) and causing cross linking at the double bond functionality. This can be done by, for example, by photocrosslinking, i.e., causing vinyl bonds to break and form cross-links by the application of radiant energy. This can be done by, for example, irradiating with a long wavelength UV lamp (365 nm, 16 watt) at room temperature while gently stirring overnight. After that, the same hardened microsphere formation and collection procedures can be used as when hydrogel is not formed at the microsphere surface.

In a further embodiment of the subject invention, a drug or other biologically active agent is loaded into the microspheres for sustained release thereof. The drug or biologically active agent can be, for example, a carrier of an aminoxyl radical or an anti-inflammatory agent (e.g., serolimos) or an antiproliferative drug (e.g., paclitaxel); a biologic; a protein; a cytokine; an oligonucleotide including antisense oligonucleotide, or a gene; a carbohydrate; hormone; etc.

When a water-soluble drug or other water-soluble biologically active agent is to be loaded, this is readily carried out by dissolving the drug or other agent in water to form an aqueous solution that is admixed with the solution formed in step (a) to form a water-in-oil emulsion that is admixed with the solution formed in step (b) to form a water-in-oil-in-water emulsion in step (c). In one embodiment, the water-soluble drug is dissolved in water at a level of about 1-500 mg per ml and the resulting solution is admixed with the solution of step (a) in a volume ratio of about 1:3 to 1:30 (aqueous solution to solution of step (a)) to form the water-in-oil emulsion.

Where an oil-soluble drug or other oil-soluble biologically active agent is to be loaded, this can be accomplished by dissolving the drug, or other agent, to be part of the solution of step (a), e.g., at a level of 1 to 500 mg/ml and the resulting solution is admixed with the solution formed in step (b) to form the admixture of step (c).

In one embodiment, the injectable microspheres of the subject invention can have a mean transverse dimension ranging from about 20 μm to about 50 μm and can be loaded with from about 4% to about 8% by weight of the microsphere of drug or other biologically active agent.

In one alternative, the surface of a PGCLM microsphere is converted to a hydrogel as described above. In another alternative, the surface of a PGCLM microsphere can be made more porous by forming micropores therein, e.g., by using laser light from a laser oscillator or by using an ultrasonic device to increase drug release rate and microsphere degradation rate.

In all cases, double bonds at the surface of the microgels can be reacted to covalently bond to a drug or other biologically active agent. Loading efficiencies (actual drug loaded (g)/theoretical load (g)×100%) are readily obtained up to about 45%, loading levels (actual loaded drug (g)/microsphere weight (g)×100%) are readily obtained up to about 8% and cumulative release in 0.1M phosphate buffered saline (PBS) at 37° is obtained up to about 50% over 50 days.

As indicated above, the injectable microspheres of the subject invention including those where hydrogel is formed at the microsphere surface, are biodegradable.

In the expression "some or each", "some" means more than one and less than all, and "each" connotes all.

The term "biodegradable" is used herein to mean capable of being broken down by various enzymes such as trypsins, lipases and lysosomes in the normal functioning of the human body and living organisms (e.g., bacteria) and/or water environment.

A third embodiment of the invention uses amphiphilic plural block copolymers to form microspheres. One block can be from PGCLM as described for the first embodiment. The other block(s) (which are hydrophilic) can be from methoxy poly(ethylene glycol) (with $M_n$ ranging from 300 to 8,000). The plural block copolymer is prepared by reacting the terminal hydroxyl of the methoxy poly(ethylene glycol) with one or more of the terminal carboxyls of the PGCLM. To form drug loaded microspheres, the amphiphilic plural block copolymer can be dissolved in a solvent for it, but not for drug, to be loaded and then the drug is added, whereby drug loaded micelle-like microspheres are formed, whereupon free drug and solvent are removed followed by drying, e.g., freeze drying. A suitable solvent for use in conjunction with a hydrophobic drug such as taxol, is dimethylformamide.

In one embodiment, the subject invention pertains to terminal functionalized three-arm glycerol poly($\epsilon$-caprolactone) microspheres (—OH, —COOH and —C═C—) as the polymer matrix that provide a long-acting, injectable drug delivery for sustained drug release over a period ranging up to a few months. The functional groups of these microspheres can be used for covalent binding of various bioactive reagents by various activation methods, through hydrophilic active chain end group —OH and —COOH as well as crosslinkable —C═C— to provide variable release profiles of for example, protein and to deliver the therapeutic agent efficiently.

Ovalbumin (OVA) is a non-toxic biodegradable protein from chicken eggs, that has been successfully used in inducing antibody (Ab) and cell-mediated immune (CMI) responses as well as for oral vaccine delivery. In one embodiment, the subject inventions provides OVA-loaded double-bond-carboxyl functionalized 3-arm poly(glycerol-co-caprolactone) maleid acid (PGCLM), hydroxyl-functional end group 3-arm poly(glycerol-co-caprolactone) (PGCL), and network NPGCLM microspheres. These can be prepared by a double emulsion technique (Price C, Stubbersfield R B, Kafrawy S E, Kendall K D, *Thermodynamics of micellization of polystyrene-block-poly(ethylene/propylene) copolymers in decane*, Britic Polyco J 1989; 21:391-4).

FIG. 1 shows a diagram of the preparation of poly(glycerol-co-caprolactone maleic acid (PGCLM) microspheres with entrapped protein ovalbumin.

Material and Methods

Materials

Ovalbumin (albumin, chicken egg; Grade V), Maleic anhydride (99%), 2,2-dimethoxy 2-phenyl acetophenone (DMPA) and sodium dodecyl suphate (SDS) were purchased from Sigma (St. Louis, Mo., USA). Prestained SDS-PAGE standards (broad range from 14 to 94 kDa and broad pI kit range from pH 3.50 to 9.50) were purchased from Bio-Rad laboratories (CA, USA) as molecular weight and isoelectric point makers. Polyvinyl alcohol (molecular weight, 12,000-23,000 of 87-89% hydrolyzed) (PVA), $\epsilon$-caprolactone and glycerol (99.0%) were purchased from Aldrich Chemical Co. (Milwaukee, Wis., USA). $\epsilon$-Caprolactone was purified by drying with $CaH_2$ for three days then distilled in vacuum at about 100° C. Glycerol was purified by distilling in vacuum. Chloroform (Mallinckrodt Baker, Paris, Ky.) was extracted with water three times to remove residual alcohol, dried with anhydrous $MgSO_4$ overnight and distilled in an atmosphere of dry argon. N,N-dimethylformamide (DMF) and triethylamine were obtained from Aldrich Chemical (Milwaukee, Wis.) and used without further purification. Osmium tetraoxide (2%) aqueous solution was purchased from Electron Microscopy Science (Fort Washington, Pa.). All other reagents were of analytical grade and used as received.

Preparation of PCL, PGCL and PGCLM

The preparation of the hydroxyl functionalised three-arm poly($\epsilon$-caprolactone) PGCL, and double-bond-functionalized three-arm poly($\epsilon$-caprolactone) ma lei c acid (PGCLM) were done according to prior published procedures (Shin I G, Kim S Y, Lee Y M, Cho C S, Sung Y K, *Methoxy polyethylene Glycol)/s-caprolactone amphiphilic block copolymeric micelle containing indomethacin: II. Micelle formation and drug release behaviours*, J Control Rel 1998; 51:13-22). In brief, the hydroxyl functionalized three arm poly($\epsilon$-caprolactone) (PGCL) were synthesized by ring-opening polymerization of $\epsilon$-caprolactone (CL) in the presence of glycerol, which acted as a core at the 20:1 feed molar ratio of CL to the hydroxyl group of glycerol and stannous octoate (0.1 wt % of CL) in a silinized Pyrox press reaction tube. After being vacuumed and refilled with dry argon several times, the polymerization tube was sealed in vacuum and placed in an oil bath at 130° C. for 48 hours. The obtained polymer was dissolved in chloroform and then gently poured into excess petroleum ether to precipitate the product. The precipitates were washed with distilled water four times and dried over $P_2O_5$ in vacuum at room temperature until a constant weight was obtained.

Secondly, PGCL and 5 equivalents of the hydroxyl functionality of maleic anhydride were placed in a three-necked flask under a dry $N_2$ environment and the flask was heated to 130° C. for one day. The reaction mixture was then cooled to room temperature and dissolved in chloroform. This chloroform solution was poured into excess petroleum ether to precipitate PGCLM. The powder precipitate was stirred in 500 mL of distilled water for 4 h for the removal of any excess maleic anhydride. After filtration, the precipitate was washed with distilled water four times and dried over $P_2O_5$ in vacuum at room temperature until a constant weight was obtained.

The linear high molecular weight PCL was also synthesized by the same method in the absence of glycerol or any other alcohol as an initiator, and the amount of stannous octoate was decreased to 0.05 wt % CL. The purpose of making high molecular weight PCL was to provide controls for the PGCL and PGCLM characterization, microspheres preparation and protein encapsulation.

Molecular weights ($M_n$) of prepared polymers were determined by gel permeation chromatography (GPC) using tetrahydrofuran (THF) as the eluent (1.0 mL/min) with a Water 510 HPLC pump, a Water U6K injector, three PSS SDV columns (linear and $10^4$ and 100 Å) in series, and a Milton ROM differential refractometer. The sample concentration was 5-10 mg/mL of THF. The columns were calibrated by polystyrene standards having a narrow molecular weight distribution.

Preparation of Microspheres

PGCLM and NPGCLM microspheres with or without OVA were prepared by the water-in-oil-in-water (w/o/w) emulsion techniques (Price C, Stubberslield R B, Kafrawy S E, Kendall K D, *Thermodynamics of micellization of polystyrene-block-poly(ethylene/propylene) copolymers in decane*, Britic Polyco J 1989; 21:391-4). In the case of PGCLM microsphere preparation, 1 mL OVA aqueous solutions (containing 40, 80 or 170 mg of OVA) were first dispersed in a 10 mL PGCLM solution (4%, 6%, 8% w/v in dichloromethane) upon vigorous stirring (900 rpm for 15 min). The resulting w/o solution was then emulsified in a 50 mL aqueous 1% PVA solution (w/v) for 30 min at 900 rpm. The resulting w/o/w emulsion was gently stirred at room temperature (22° C.) by a magnetic stirrer (EYELA Magnetic stirrer RC-2) overnight to evaporate the organic solvent.

The resultant sample was collected by centrifugation at 22° C. (International Centrifuges, Clinical Model, International Equipment Co. Needham Hts, Mass. 02194 USA) and washed with distilled water at least four times to remove the PVA emulsifier. The sample was freeze-dried for 3 days in a Virtis Freeze Drier (Gardiner, N.Y.) under vacuum at −45° C. to obtain the microspheres, which were stored in vacuum desiccators at 4° C. before characterization and use.

To prepare microspheres which would have a crosslinked surface network structure (NPGCLM), a photo-initiator, DMPA, of 0.1% (w/w) of the PGCLM was added to the initially formed w/o PGCLM emulsion and then emulsified in 1% PVA solution to form w/o/w solution. This w/o/w solution was then irradiated by a long wavelength UV lamp (365 nm, 16 watt) at room temperature upon gently stirring overnight. After that, the same collection procedures as PGCLM microspheres preparation were used to collect NPGCLM microspheres.

Microspheres Characterization
Fourier Transform Infrared (FTIR)

Fourier transform in infrared (FTIR) spectra were obtained from a Nicolet Magna-IR 560 spectrophotometer (Madison, WT). Two mg PGCLM or NPGCLM microspheres were finely grinded with 15 mg KBr and compressed into pellets for IR scanning in the range from 400 to 4000 cm$^{-1}$ with a resolution of 8 cm$^{-1}$ and carbon black reference. The detector was purged carefully by clean dry helium gas to increase the signal level and to reduce moisture contamination.

Differential Scanning Calorimetric (DSC)

Differential scanning calorimetric (DSC) data were obtained from a thermal analysis data system (DSC, 2920, TA Instrument). The DSC was calibrated using indium as the standard. Samples (1-3 mg) were heated in sealed aluminum pans from −110 to 190° C. at a scanning rate of 10° C./min under nitrogen purge, with an empty aluminum pan as a reference. The degree of crystallinity was obtained from the first scan (10° C./min), while the melting temperature was from the second scan at 20° C./min after cooling from the first scan to RT. The heat of fusion ($\Delta H_m$) was determined by integrating the normalized area of melting endotherms. The degree of crystallinity ($X_c$) of the synthesized polymer was then calculated according to the following equation:

$$Xc = (\Delta H_{m\ sample} / \Delta H°_{m, 100\% crystalline}) \times 100\%.$$

where $\Delta H°_m$ is the theoretical heat of fusion of PCL (135 J/g). During the temperature range from −110 to 190° C., no $T_g$ was observed for the synthesized polymers.

Scanning Electron Microscopy (SEM)

The exterior and interior morphology of the PGCLM microspheres was analyzed by scanning electron microscopy (SEM). In brief, 5.0 mg of freeze-dried microspheres were dispersed in 500 µL of distilled water, placed onto the top flat surface of metal stubs and air-dried. The samples were sputtering coated (Edwards, S150B, Sussex, UK) for 30 s and viewed under a STEREO SCAN 440 electron microscope (JEOL samples were LTD. TOKYO, JAPAN0 at 25 kV.

Backscattered Electron Imagines

Backscattered electron imagines with osmium tetraoxide (OsO$_4$) staining technique was used to qualitatively assess the presence of the >C═C< functional groups on the surface of PGCLM microspheres. Due to the attachment of OsO$_4$ onto the >C═C< bonds and hence their labeling by heavy element Os, these double bond regions on the surface of the PGCLM microsphere could be visually assessed by backscattered electrons for Os element.

In brier, PGCLM microspheres were placed on aluminum stubs by double-sided adhesive tapes. The mounted microspheres were treated with osmium tetraoxide (2%) vapor for overnight in an enclosed container for the attachment of OsO$_4$ onto the >C═C< bonds on PGCLM microsphere surface. After residual OsO$_4$ vapor was removed, the OsO$_4$ treated microspheres were then placed in a putter carbon coater (Edwards, Auto 306 High Vacuum Evaporator, Edwards High Vacuum International, Wilmington, Mass.) for 30 s to produce a carbon coating of approximately 150 Å in thickness onto PGCLM microspheres. The coated microspheres were viewed under a STEREO SCAN 440 (JEOL samples were LTD.TOKYO, JAPAN) for backscattered electron imagines recording by a Tracor Northern energy-dispersive X-ray analysis (Middleton, Wis.). The Os peaks at 1.93 $M_\alpha$ and 8.91 $L_\alpha$ were used to determine the presence of Os and hence >C═C< regions on PGCLM microsphere surface.

Particle Size Analysis

The particle size and size distribution of the prepared microspheres were measured by the laser light scattering method (Brinkmann Particle Size Analyzer 2010, Brinkmann Instruments, Inc., Cantiague Road, Westbury, N.Y. 11590). The dried microsphere powder samples were first suspended in HPLC grade water (5-10% vol.) and then slightly sonicated for achieving a homogeneous suspension before size measurement. The data obtained included volume density percentage, mean diameter and size distribution of the microspheres.

Microsphere Encapsulation of Albumin and In Vitro Release
Encapsulation Efficiency Determinations The amounts of OVA entrapped within PGCLM microspheres were measured by dissolving 100 mg of the OVA loaded microspheres prepared as described above in 2.0 mL of dichloromethane and the OVA in the solution was extracted three times by 2.0 mL of double-distilled water. The OVA content of the extraction solution was determined by using a UV-Visible spectroscopy absorbance at 280 nm and a standard calibration curve from known concentrations of OVA solutions. The OVA standard calibration curve is linear in the 1-100 µg/mL concentration range with a correlation coefficient of 0.998. The amount of OVA encapsulated in the PGCLM or NPGCLM microspheres, i.e. loading level in %, indicates the amount of OVA in mg encapsulated per 100 mg of the microspheres. Also, the loading efficiency of the process is defined as the ratio in % of actually loaded OVA within 100 mg microspheres to the initial feed OVA amount during the preparation of microspheres.

In Vitro OVA Release Study

In vitro ovalbumin (OVA) release profiles were obtained by incubating OVA-loaded microspheres (5 mg) in a centrifuge test tube containing 5 mL of phosphate-buffered saline solution (pH 7.4) and 0.05% (w/v) of sodium azide used as preservative, at 37° C. At predetermined time intervals (50 days), the microsphere suspension was centrifuged at 700 rpm for 10 min and the supernatant was collected. The concentration of OVA in the supernatant was measured by a PERKIN Elmer Lambda 2 UV/VIS spectrometer (Norwalk, Conn.) at the wavelength 280 nm. Results were expressed as the cumulative ovalbumin released percentage.

The test tube was replaced by fresh phosphate buffer to maintain at a constant volume. Each experiment was conducted in triplicate. To determine whether there would be any residual OVA adhering onto the microsphere surface after centrifugation, a control experiment was conducted by centrifuging a mixture of OVA solution and OVA loaded microspheres according to the same centrifugation condition above. The data of this control experiment indicated negligible quantity of OVA residue remaining on the microspheres surface.

Stability of OVA Encapsulated in Microspheres The stability of OVA released from microspheres was analyzed by SDS-polyacrylamide gel electrophoresis (SDS-PAGE). The amount of OVA was qualitatively assessed by comparing with a standard OVA marker according to the method of Laemmli (Kim S Y, Lee Y M, *Methoxy poly(ethylene glycol)/poly(s-caprolactone) amphiphilic block copolymeric nanosphere containing indomethacin: III. Pharmacokinetic study in rat*. J Contr Rcl. Submitted for publication). Briefly, the released OVA samples were dissolved in a buffer containing 2% SDS, 0.5% β-mercaptoethanol, 6% sucrose, and 10 mM bromophenol blue. After the samples were boiled for 5 minutes and cooled down on ice for 1-2 minutes, they were loaded immediately in a 10% SDS-PAGE gel. The gel was run at 20-30 mA until the dye reached the front line. The gel was stained in coomassie blue solution and destained until the proteins were clearly seen. For each sample, two concentrations (2 μg/lane and 4 μg/lane) of OVA were used.

All patents, patent applications, provisional applications, and publications referred to or cited herein are incorporated by reference in their entirety, including all figures and tables, to the extent they are not inconsistent with the explicit teachings of this specification.

The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available from known sources, e.g., chemical supply houses, so no details are given respecting them Example 1

PGCL-Ma-3 solutions in dichloromethane were made up containing 2% w/v polymer (denoted PGCLM21), 4% w/v polymer (denoted PGCLM41), 6% w/v polymer (denoted PGCLM61) and 8% w/v polymer (denoted PGCLM 81).

An ovalbumin protein (albumin, chicken egg, Grade V), denoted OVA, was selected to represent drug to be loaded. It has been used as an antigen in inducing antibody, cell-mediated immune responses, as well as for oral vaccine delivery.

1 ml OVA aqueous solutions containing 10, 40 or 85 mg OVA were dispersed in 10 ml of PGCLM solution with vigorous stirring (900 rpm for 15 minutes with a magnetic stirrer) to form a water-in-oil emulsion where aqueous OVA solution was the disperse phase in PGCLM solution continuous phase. The resulting w/o emulsion was emulsified in 50 ml aqueous 1% PVA($M_n$=12,000-23,009 87-89% hydrolyzed) solution (w/v) by mixing for 30 minutes at 900 rpm with a magnetic stirrer to form a w/o/w emulsion. The resulting w/o/w emulsion was gently stirred overnight at 40% by a magnetic stirrer (EYELA Magnetic stirrer RC-2) to evaporate the solvent leaving hardened microspheres loaded with OVA, undissolved in the aqueous continuous phase.

The microspheres were collected by centrifugation at 22° C. (International Centrifuge, Clinical Model, International Equipment Co. Needham Hts, Mass. 02194 USA) and washed with distilled water at least four times to remove PVA emulsifier. The sample was then freeze-dried for 3 days in a Virtis Freeze Drier (Gardiner, N.Y.) under vacuum at 45° C. to obtain the microspheres which were stored in vacuum dessicators at 40° C. before characterization and use.

In another case, the procedure was the same as above but DMPA at 0.1% (w/w of PGCLM) was added to the solution of PGCLM before it was used to form the w/o emulsion with the aqueous solution of OVA whereupon the w/o emulsion was admixed with the PVA aqueous solution to form a w/o/w emulsion which was irradiated by using a long wavelength UV lamp (365 nm, 16 watts) at room temperature with gentle stirring overnight. After that, the same procedure as used above, was used to collect the microspheres. The result was cross-linked surface network structure microspheres denoted NPGCLM.

Characteristics of OVA-loaded PGCLM and NPGCLM microspheres are shown in the following tables.

TABLE 1

Physicochemical characteristics of hydroxyl-functionalized poly (glycerol-co-caprolactone) (PGCL) and double-bond-functionalized poly(glycerol-co-caprolactone) maleic acid (PGCLM) Polymers

| Polymer | Mn (kg/mol)[a] | $T_g$ (° C.) | $T_m$ (° C.) | ΔHm (J/g) | Xc (%)[b] |
|---|---|---|---|---|---|
| PGCL[c] | 15.4 | — | 52.5 | 61.3 | 45.4 |
| PGCLM[d] | 13.3 | — | 48.9 | 64.8 | 48.0 |
| NPGCLM | 13.3 | — | 51.3 | 47.3 | 35.0 |
| PCL | 56.9 | −59 | 59 | — | 52[28] |
| PCL-O | 39.1 | −54 | 52 | — | 47[28] |

[a]Determined by GPC with polystyrene standards.
[b]Xc = (ΔH$_{m\ sample}$/ΔH °$_{m,\ 100\%\ crystalline}$) × 100%.
[c]CL/OH is the molar ratio of CL monomer to hydroxyl and is calculated by (mol of CL)/3 × mol of glycerol., 20/1
[d]PGCL-OH and 5 equiv of the hydroxyl functionality of maleic anhydride molar ratio.

TABLE 2

Characteristics of OVA-loaded PGCL, PGCLM and NPGCLM microspheres

| Code | Polymer[a] (%, w/v) | OVA con. (mg) | PVA[b] (%, w/v) | DCM/ H2O (v/v) | Mean Diam. ($d_{vs}$, μm) | OVA loading | Loading Efficiency (%)[c] |
|---|---|---|---|---|---|---|---|
| PGCLM21 | 2 | 40 | 1 | 1/20 | 16.8 | 5.7 | 38.3 |
| PGCLM41 | 4 | 40 | 1 | 1/20 | 18.0 | 6.0 | 41.1 |
| PGCLM61 | 6 | 40 | 1 | 1/20 | 19.2 | 7.6 | 42.2 |
| PGCLM81 | 8 | 40 | 1 | 1/20 | 21.0 | 4.1 | 43.2 |
| PGCL61 | 6 | 40 | 1 | 1/20 | 34.3 | 7.2 | 36.2 |
| NPGCLM61 | 6 | 40 | 1 | 1/20 | 21.9 | 4.2 | 45.3 |

[a]Dichloromethane as solvent, PGCL Mn = 15,400; PGCLM Mn = 13,300; NPGCLM Mn = 13,200
[b]Water as solvent
[c]Loading efficiency = Actual load (g)/Theoretical load (g) × 100%

The influence of OVA concentration on OVA loading efficiencies is shown in Table 3.

TABLE 3

Influence of Ovalbumin concentration on OVA loading efficiency of microspheres

| Code | OVA Conc. (mg/ml, H$_2$O) | Polymer Conc. (%, w/v) | PVA (%, w/v) | OVA loading (%) | Mean Diameter ($d_{vs}$, μm) | Loading Efficiency[a] (% w/w) |
|---|---|---|---|---|---|---|
| PGCLM61-1 | 10 | 6 | 1 | 1.4 | 17 | 43.0 |
| PGCLM61-2 | 40 | 6 | 1 | 6.0 | 19.2 | 38.3 |
| PGCLM61-3 | 85 | 6 | 1 | 8.1 | 16 | 28.7 |

[a]Loading efficiency = Actual load (%)/Theoretical load (%) × 100%

The influence of PVA concentration on OVA loading efficiencies is shown in Table 4.

TABLE 4

Influence of PVA concentration on OVA loading efficiency of microspheres

| Code | OVA Conc. (mg/ml, $H_2O$) | Polymer Conc. (%, w/v) | PVA (%, w/v) | OVA loading (%) | Mean Diameter ($d_{vs}$, µm) | Loading Efficiency$^a$ (% w/w) |
|---|---|---|---|---|---|---|
| PGCLM61-4 | 80 | 6 | 0.5 | 1.4 | 26 | 32.7 |
| PGCLM61-2 | 80 | 6 | 1 | 6.0 | 28.2 | 38.3 |
| PGCLM61-5 | 80 | 6 | 5 | 7.4 | 24 | 26.7 |

$^a$Loading efficiency = Actual load (g)/Theoretical load (g) × 100%

The molecular weights and polydispersities are determined by gel permeation chromatography using polystyrene standards. More particularly molecular weights of prepared polymers ($M_n$) are determined by gel permeation chromatography (GPC) using tetrahydrofuran (THF) as eluant (1.0 ml/min) with a Water 510 HPLC pump, a Water U6K injector, three PSS SDV columns (linear and $10^4$ and 100 angstroms) in series, and a Milton ROM differential refractometer, and the sample concentration is 5-10 mg/ml of THF and the columns are calibrated by polystyrene standards having a narrow molecular weight distribution.

It should be understood that this example and embodiment described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for preparing a hardened biodegradable microsphere wherein said method comprises
    (a) dissolving a double bond functionalized polyhydric alcohol ester of polyester in a hydrophobic organic solvent,
    (b) dissolving a stabilizer in water,
    (c) admixing the solutions formed in step (a) and step (b) to form an emulsion where the solution formed in step (b) constitutes the continuous phase and the solution formed in step (a) constitutes the disperse phase,
    (d) evaporating the organic solvent to form a hardened microsphere by polymer precipitation, from the double bond functionalized polyhydric alcohol ester,
    (e) recovering the microsphere.

2. The method, according to claim 1, wherein the stabilizer s a polyalcohol.

3. The method, according to claim 1, wherein the stabilizer is dextran.

4. The method, according to claim 1, wherein the stabilizer is a sucrose ester.

5. The method of claim 1 where the double bond functionalized polyhydric alcohol ester is obtained by polymerizing ε-caprolactone monomer or a blend of ε-caprolactone monomer and lactide monomer or glycolide monomer in the presence of polyhydric alcohol containing from 3 to 6 hydroxyl groups to form polyhydric alcohol ester where the acyl groups contain free hydroxyl at their terminal ends and reacting with maleic anhydride to convert some or each of the free hydroxyls to moiety containing 2-carboxy ethenyl group.

6. The method of claim 1 where the double bond functionalized polyhydric alcohol ester is obtained by polymerizing ε-caprolactone monomer in the presence of glycerol to form the polyhydric alcohol ester where the acyl groups contain free hydroxyl at their terminal ends and reacting with maleic anhydride to convert some or each of the free hydroxyls to moiety containing 2-carboxy ethenyl group.

7. The method of claim 1 where the double bond functionalized polyhydric alcohol ester has a number average molecular weight, $M_n$, ranging from 1,000 to 50,000.

8. The method of claim 1 where the solvent is one that dissolves the double bond functionalized polyhydric alcohol ester at room temperature and has a boiling point ranging from 30-45° C.

9. The method of claim 8 where the solvent is dichloromethane.

10. The method of claim 1 where the volume ratio of solution formed in step (b) to solution formed in step (a) admixed in step (c) ranges from 3:1 to 10:1.

11. The method of claim 1 where a photoinitiator is included in the solution formed in step (a) and the admixture formed in step (c) is irradiated to obtain photocrosslinking to provide hydrogel surface on disperse phase particles.

12. The method of claim 1 where water soluble drug or other biologically active agent is dissolved in water to form an aqueous solution which is admixed with solution formed in step (a) to form a water in oil emulsion which is admixed with the solution formed in step (b) to form a water in oil in water emulsion in step (c).

13. The method of claim 1 where oil soluble drug or other biologically active agent is present in the solution formed in step (a).

14. The method, according to claim 1, wherein a double bond functionalized poly (ortho ester) is prepared by the reaction between the diketene acetal 3,9-diethylidene-2,4,8,10 tetraoxaspiro[5.5] undecane and 1,10-decanediol or triethylene glycol.

15. An injectable hardened microsphere, in the absence of any organic solvent, having a mean transverse dimension from 5 to 200 µm, formed from multiarm biodegradable polymers wherein the surface of the microsphere is hydrophilic and comprises unsaturated C=C bonds, wherein said microsphere is formed from a double bond functionalized polyhydric alcohol ester of polyester, and wherein said microsphere is loaded with from 0.1 to 25% by weight of the microsphere of a drug or other biologically active agent for sustained release after injection of the microsphere and wherein the surface of the microsphere has micropores formed therein.

16. A drug-loaded hardened microsphere, in the absence of solvent, formed from an amphiphilic plural block copolymer where one block is from glycerol poly(ε-caprolactone) maleic acid and the other block(s) are from methoxy poly (ethylene glycol), wherein said microsphere is formed by dissolving the copolymer in organic solvent, adding the drug to the formed solution, then removing free drug and solvent and then drying.

* * * * *

UNITED STATES PATENT AND TRADEMARK OFFICE
CERTIFICATE OF CORRECTION

| | | |
|---|---|---|
| PATENT NO. | : 8,092,835 B1 | |
| APPLICATION NO. | : 13/269738 | |
| DATED | : January 10, 2012 | |
| INVENTOR(S) | : Daqing Wu et al. | |

It is certified that error appears in the above-identified patent and that said Letters Patent is hereby corrected as shown below:

Column 9,
Line 26, "transform in infrared" should read --transform infrared--

Signed and Sealed this
Twenty-seventh Day of March, 2012

David J. Kappos
*Director of the United States Patent and Trademark Office*